US008529848B2

(12) United States Patent
Danehy et al.

(10) Patent No.: US 8,529,848 B2
(45) Date of Patent: Sep. 10, 2013

(54) SYSTEMS AND METHODS FOR TRANSFER OF LIQUID SAMPLES

(76) Inventors: Ronald Danehy, Shirley, MA (US); Jorge Fonseca, East Palo Alto, CA (US); Jayanthi Prasad, Lexington, MA (US)

( * ) Notice: Subject to any disclaimer, the term of this patent is extended or adjusted under 35 U.S.C. 154(b) by 13 days.

(21) Appl. No.: 13/170,563

(22) Filed: Jun. 28, 2011

(65) Prior Publication Data

US 2011/0318241 A1    Dec. 29, 2011

Related U.S. Application Data

(60) Provisional application No. 61/359,320, filed on Jun. 28, 2010.

(51) Int. Cl.
*B01L 3/02* (2006.01)

(52) U.S. Cl.
USPC ........ 422/501; 422/509; 422/521; 73/863.32; 73/863.33; 73/864; 73/864.01; 73/864.11; 73/864.16; 73/864.17

(58) Field of Classification Search
USPC ............... 422/501, 509, 511, 521, 524–525, 422/63–68.1, 921; 73/863.32, 864, 864.01, 73/864.11, 864.13, 864.14, 864.16–864.18
See application file for complete search history.

(56) References Cited

U.S. PATENT DOCUMENTS

| | | | |
|---|---|---|---|
| 5,443,791 A | 8/1995 | Cathcart et al. | |
| 5,763,263 A | 6/1998 | Dehlinger et al. | |
| 6,132,582 A | 10/2000 | King et al. | |
| 6,143,252 A * | 11/2000 | Haxo et al. | 506/40 |
| 6,589,483 B1 * | 7/2003 | Maeda | 422/525 |
| 6,824,024 B2 | 11/2004 | Ingenhoven et al. | |
| 7,105,129 B2 | 9/2006 | Ruddock | |
| 7,628,960 B2 | 12/2009 | Ruddock | |
| 7,682,568 B2 * | 3/2010 | Jarvimaki et al. | 422/500 |
| 2001/0019845 A1 | 9/2001 | Bienert et al. | |
| 2003/0215360 A1 | 11/2003 | Ruddock | |
| 2005/0244303 A1 * | 11/2005 | Ingenhoven et al. | 422/100 |
| 2006/0105453 A1 | 5/2006 | Brenan et al. | |
| 2007/0053797 A1 | 3/2007 | Muraishi et al. | |
| 2007/0196238 A1 | 8/2007 | Kennedy et al. | |
| 2009/0110606 A1 * | 4/2009 | Fukushima | 422/100 |

OTHER PUBLICATIONS

PCT/US2011/042176, "International Search Report mailed Feb. 24, 2012", 3 Pgs.
PCT/US2011/042176, "Written Opinion mailed Feb. 24, 2012", 5 Pgs.

* cited by examiner

*Primary Examiner* — Brian R Gordon

(57) ABSTRACT

A system for preparing biological sample contains a body including a proximal side and a distal side, a plurality of mandrels, a plurality of resilient elements, a plurality of fluid dispensers, and one or more samples. The mandrels are moveably positioned within the body, where each resilient element engages a respective one of the mandrels. Each of the fluid dispensers is configured to engage a distal end of a corresponding one of the mandrels. Each sample comprises a solution containing one or more nucleic acid sequences contained within at least one of the fluid dispensers.

15 Claims, 9 Drawing Sheets

FIG. 5
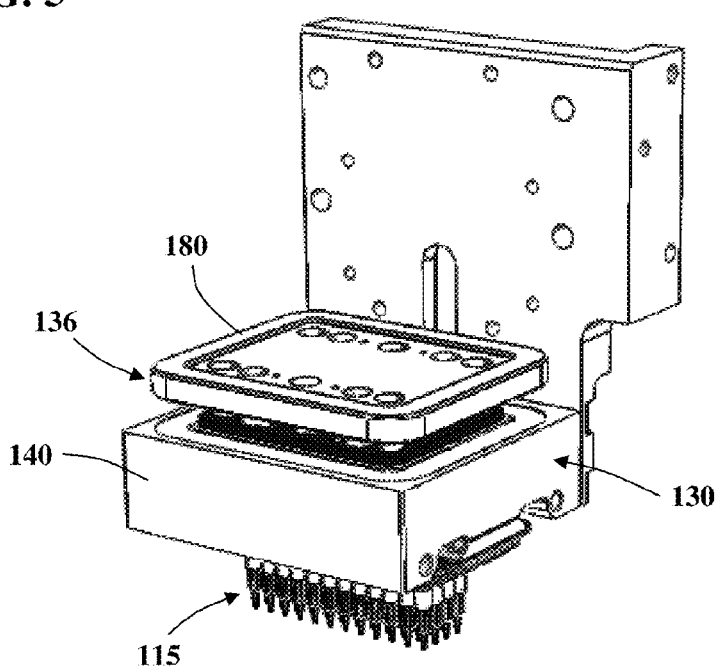
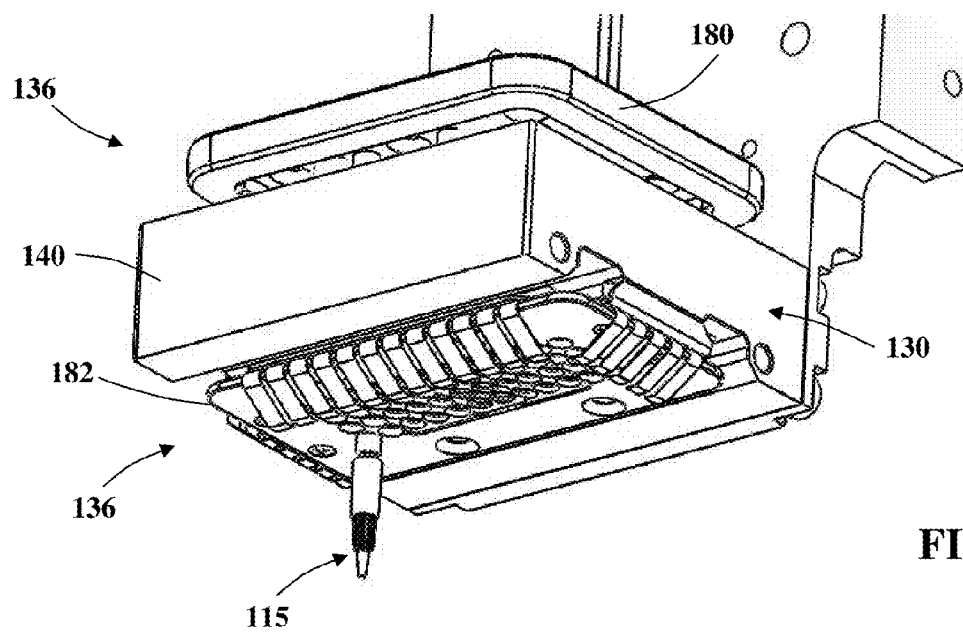
FIG. 6

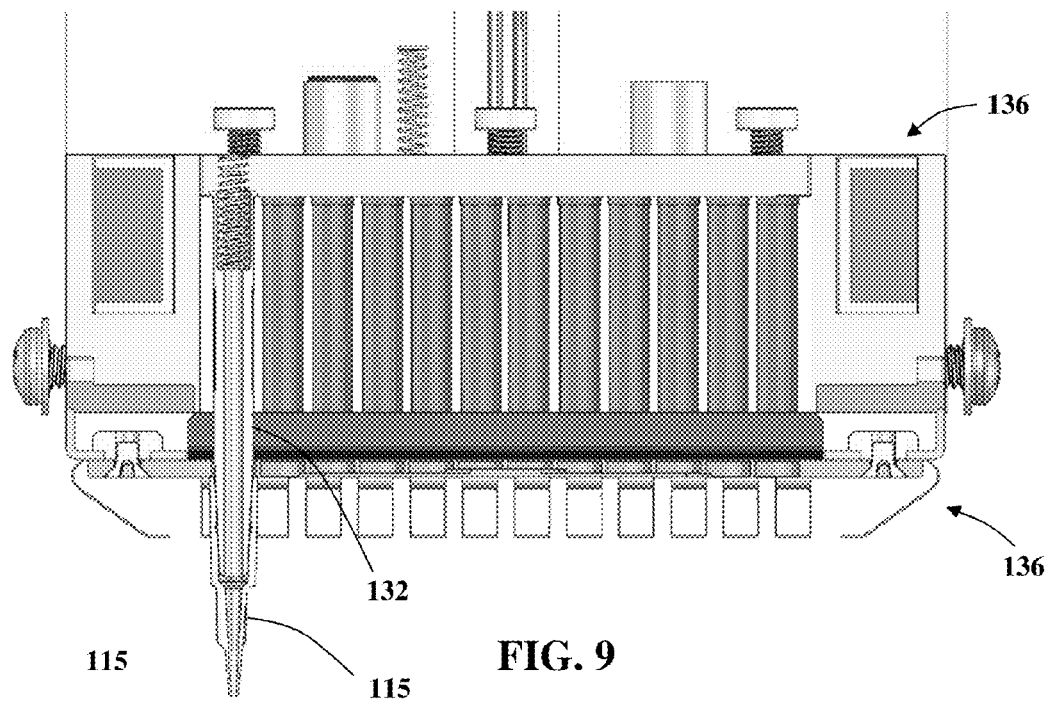
FIG. 9
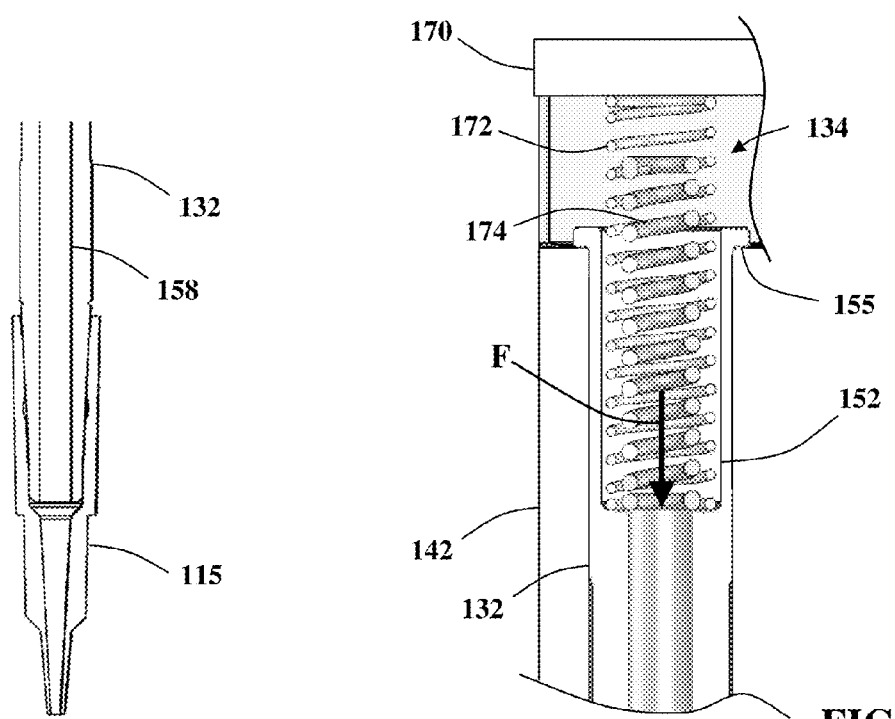
FIG. 10
FIG. 11

SYSTEMS AND METHODS FOR TRANSFER OF LIQUID SAMPLES

BACKGROUND OF THE INVENTION

1. Field of the Invention

The present invention relates generally to loading systems and methods, such as loading systems and methods for transferring liquid samples between a supply source to a sample carrier.

2. Description of the Related Art

Microfluidics control involves the transfer of small quantities of fluids through a system or between two or more locations. For example, in the field of biochemistry, precise control of the transfer of small quantities of assay, reagent, and/or biologically active fluids into a card, plate, or similar holding means is needed in preparation for a test or measurement.

In recent years, the desire to increase the number of samples that can be analyzed during a single run has resulted in a push to ever smaller sample volumes. In such cases, the quantity of fluid being transferred into or onto a sample plate or card may be in the microliter or nanoliter range.

For example, a multi-through-hole plate for high throughput screening, testing, and/or amplification of nucleic acid sequences or other biological samples has been developed that holds at least 3000 sample wells. Precise and consistent filling between the various sample wells on a single plate, or multiple plates, may aid in providing more accurate results that also allow better comparison and correlation between measurements for each of the samples.

In light of the current state of the art, systems, devices, and methods are desirable to provide accurate, consistent transfer of small quantities of liquid samples for processing and testing.

SUMMARY OF THE INVENTION

Embodiments of the present invention are generally directed to improved devices, systems, and methods for transferring small quantities of fluids between a source and a carrier configured to receive the fluid. Embodiments of the present invention find particular use where large numbers of receiving containers or wells on the order of thousand of samples per experiment or run are desirable, for example, for performing gene sequencing, amplification procedures (e.g., polymerase chain reaction (PCR), real-time PCR), and the like.

While embodiments and examples disclosed herein are primarily directed to biochemistry applications, it will be appreciated that embodiments of the present invention may also find utility in other applications. For instance, the present invention is useful where transfer of small and/or accurate quantities of fluids is desirous and/or where large numbers of sample volumes are needed or desired.

Each and every feature described herein, and each and every combination of two or more of such features, is included within the scope of the present invention provided that the features included in such a combination are not mutually inconsistent. Additional aspects, features, and advantages of the present invention are set forth in the following description and claims, particularly when considered in conjunction with the accompanying drawings in which like parts bear like reference numbers.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIG. 5 is a top perspective view of a delivery sub-system according to an embodiment of the present invention.

FIG. 6 is a bottom perspective view of the delivery sub-system shown in FIG. 5.

FIG. 9 is a cross-sectional view of the interior of the delivery sub-system shown in FIG. 5.

FIG. 10 is cross-sectional view a fluid dispenser and the distal end of a mandrel of the fluid dispenser shown in FIGS. 3 and 5.

FIG. 11 is a magnified view of the proximal end of the mandrel shown in FIG. 10 and showing engagement with a non-linear resilient element according to an embodiment of the present invention.

DETAILED DESCRIPTION OF THE DRAWINGS

Figure 1:
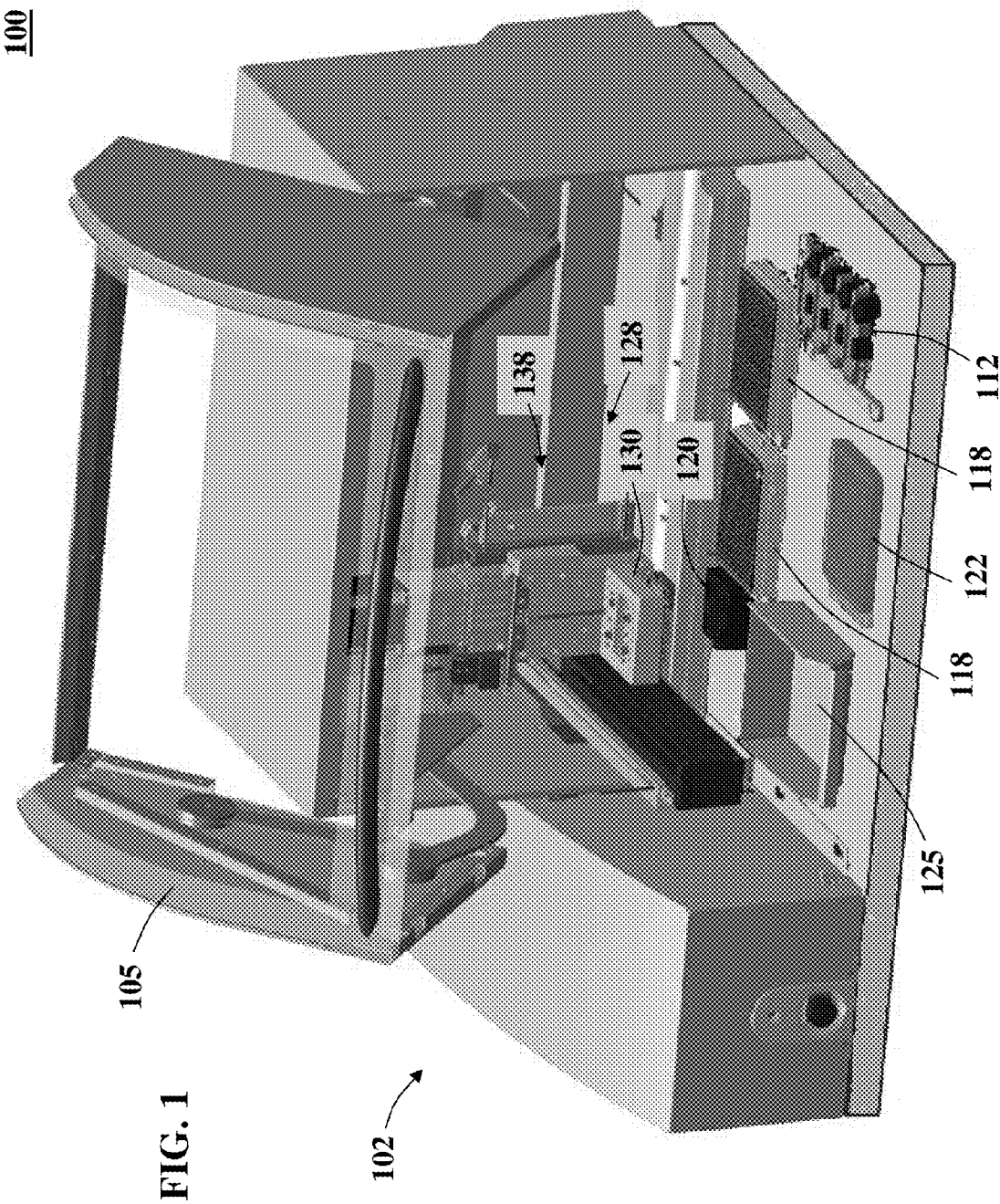
FIG. 1 is a perspective view of system according to an embodiment of the present invention for loading or transferring a liquid sample.

Referring to FIG. 1, a loading system 100 according to an embodiment of the present invention is illustrated. Loading system 100 comprises an enclosure 102 maintaining loading system 100 in a clean and controlled environment during operation. Enclosure 102 includes a door, window, or access portal 105. As shown in FIG. 1, door 105 may have an open position (as shown in FIG. 1) for providing access to loading system 100 and a closed position (not shown) for providing the controlled environment.

Figure 2:
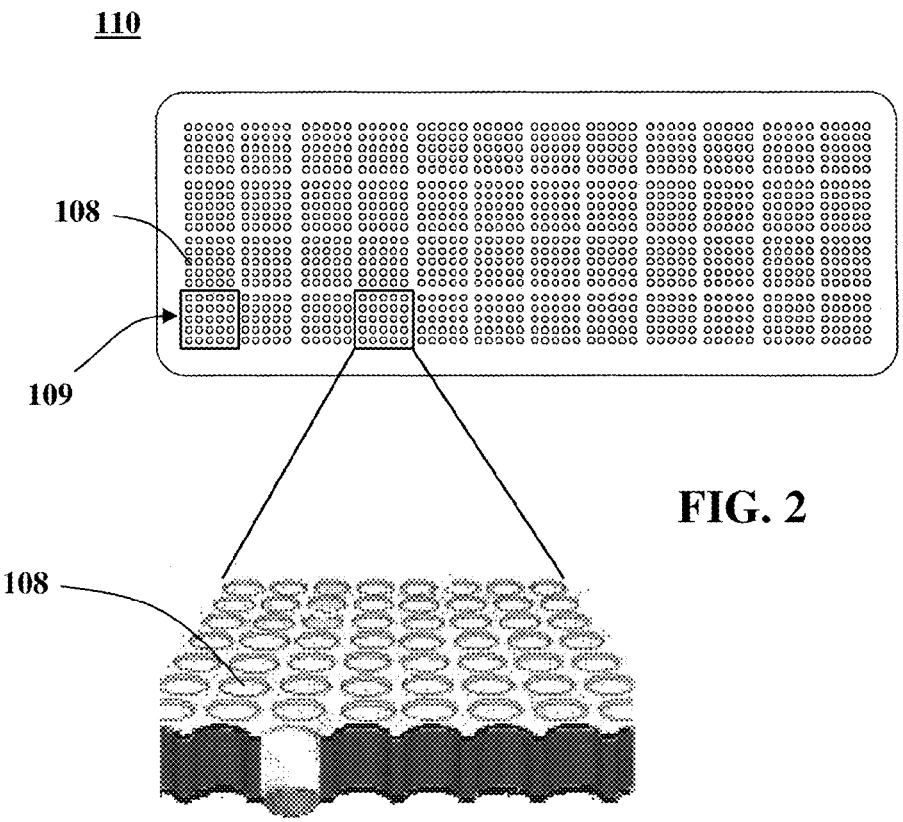
FIG. 2 is a drawing of a sample array according to an embodiment of the present invention and suited for use in the system shown in FIG. 1

With additional reference to FIG. 2, system 100 includes various components and subsystems for accurately loading or transferring one or more fluids into a plurality of receptacles 108 of one or more sample arrays 110. For example, system 100 may include a sample array platform or support 112 for maintaining or securing one or more sample arrays 110 in a fixed and/or known position for processing by loading system 100.

Figure 3:
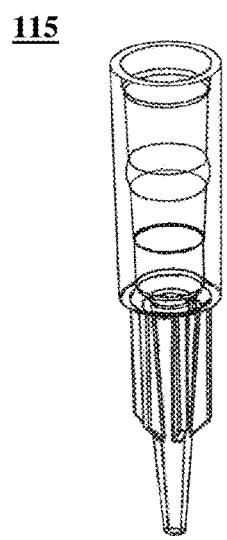
FIG. 3 is a perspective view of a fluid dispenser according to an embodiment of the present invention and suited for use in the system shown in FIG. 1
Figure 4:
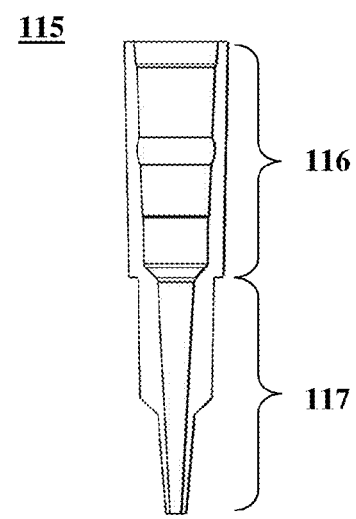
FIG. 4 is a cross-sectional view of the fluid dispenser shown in FIG. 3.

With additional reference to FIGS. 3 and 4, system 100 also includes various stations, platforms, and the like for processing groups or sets of fluid dispensers 115 which may be loaded with one or more fluids or solutions for transfer to the sample arrays 110. For example, system 100 may comprise one or more fluid dispenser holders 118, configured to maintain fluid dispensers 115 in condition for engagement by system 100 during operation and a fluid dispenser registration station or set plate 120. System 100 may further include a fluid dispenser fill station, e.g., a microtiter plate, sample dish, or sample plate 122, which may be used to fill fluid dispensers 115, and a disposal bin 125 for receiving fluid dispensers 115 after use.

With further reference to FIGS. 5-8, system 100 may comprise a delivery system 128 that includes a head assembly 130, a plurality of mandrels 132, a resilient element 134, a stripper or stripping mechanism 136. System 100 may also include a positioner 138 that to move and position delivery system 128 within enclosure 102. Head assembly 130 comprises a frame 140 and a head, insert, or block 142 that may be mounted or attached to frame 140, head assembly 130 having a proximal side 145 and a distal side 148. In the illustrated embodiment, delivery system 128 holds as many as 48 fluid dispensers at one time, with each fluid dispenser 115 being able to service one subzone of receptacles 108 on sample array 110.

In certain embodiments, the system 100 is part of a larger system used to perform biological/microbiological testing or processing. For example, a system according to embodiments of the present invention may comprise one or more sample arrays 110, one or more biological samples or assays, the system 100 for transferring, loading, or depositing the samples or assays into the one or more sample arrays, and/or a testing or processing system such as a gene sequencing system or instrument or an amplification system or instrument (e.g., a system or instrument for use in a traditional polymerase chain reaction (PCR), real-time PCR (qPCR), digital PCR (dPCR), and/or, or the like).

Sample array 110 may comprise any of the various formats known in the art for providing relatively large numbers of biological or other types of samples for testing. The sample arrays may be configured or suitable for various types of biological/microbiological testing or processing, such as gene sequencing, and/or amplification processes, or the like. In certain embodiments, system 100 may be used to dispose samples onto the surface of a card, substrate, microchip, or the like. In other embodiments, system 100 is used to deposit one more solution samples into wells, channels, through-holes, or the like of a card or plate. For example, referring again to FIG. 2, system 100 may be used to transfer one or more samples to the various open receptacles 108 in sample array 110. Examples of suitable sample arrays are disclosed in U.S. Pat. Nos. 6,306,578, 7,682,565, 7,687,280 and US Patent Application Publication 2009/0081768 U.S. Pat. No. 7,687,280, all of which are herein incorporated by reference in their entirety as if fully set forth herein.

For instance, U.S. Pat. No. 6,027,873 discloses a method for holding samples for analysis and an apparatus thereof includes a testing plate with a pair of opposing surfaces and a plurality of holes. Each of the holes extends from one of the opposing surfaces to the other one of the opposing surfaces. The holes are arranged in groups, where each group has at least two rows and two columns of holes. The groups are arranged in sets, where each set has at least two rows and two columns of groups. To analyze samples, at least one of the opposing surfaces of the testing plate is immersed in a solution to be analyzed. A portion of the solution enters openings for each of the holes in the immersed opposing surface. Once the holes are filled with solution, the testing plate is removed and is held above a supporting surface. Surface tension holds the solution in each of the holes. The solution in one or more of the holes is then analyzed and the solution in one of these holes is identified for further study. The location of the identified solution is marked based upon its location within a particular set and group of holes.

U.S. Pat. No. 6,387,331 discloses a system and method for analyzing a plurality of liquid samples. The system has a platen having two substantially parallel planar surfaces and a plurality of through-holes dimensioned so as to maintain a liquid sample in each through-hole by means of surface tension. A source of optical radiation illuminates the through-holes, and an optical arrangement analyzes the light emanating from the through-holes. The through-holes may be individually addressable, and may have volumes less than 100 nanoliters. Samples may be drawn from a planar surface by capillary action and may be accurately dispensed, diluted and mixed in accordance with embodiments of the invention.

U.S. Pat. No. 7,332,271 discloses apparatuses and methods for conducting multiple simultaneous micro-volume chemical and biochemical reactions in an array format. In one embodiment, the format comprises an array of microholes in a substrate. Besides serving as an ordered array of sample chambers allowing the performance of multiple parallel reactions, the arrays can be used for reagent storage and transfer, library display, reagent synthesis, assembly of multiple identical reactions, dilution and desalting. Use of the arrays facilitates optical analysis of reactions, and allows optical analysis to be conducted in real time. Kits may comprise a microhole apparatus and a reaction component of the method(s) to be carried out in the apparatus.

The sample arrays may be made by various known. For instance, the sample arrays may be made according to the processes disclosed in Published U.S. Application No. 20060105453, which is incorporated herein by reference in its entirety. U.S. Application No. 20060105453 discloses a differentially coated device for conducting a plurality of nano-volume specified reactions, the device comprising a platen having at least one exterior surface modified to a specified physicochemical property, a plurality of nano-volume channels, each nano-volume channel having at least one interior surface in communication with the at least one exterior surface that is selectively coated with an optionally dissolvable coating agent physisorbed to at least one interior surface, wherein the optionally dissolvable coating agent comprises a coating agent and a first component for the plurality of specified reactions. Methods for preparing and using such devices are also provided, as well as a method of registering a location of a dispenser array in relation to a microfluidic array. A first one of the dispenser array and the microfluidic array is movable in relation to the frame, and the other of the first one of the dispenser array and the microfluidic array is fixed relative to the frame. Quantities related to a vector displacement from the alignment position to a fixed position on the one of the dispenser array and the microfluidic array is determined. The quantities thus determined are used to guide positioning of the dispenser array relative to the microfluidic array. The sample arrays of U.S. Application No. 20060105453 may be used in the systems and methods of the present invention.

Referring again to FIG. 2, sample array 110 of the illustrated embodiment includes a plurality of subzones or sub-arrays 109, wherein each subzone 109 may comprise a 4×4 array of small through-holes 108. Alternatively, subzones 109 may comprise an array of 5×5, 6×6, 8×8, or higher number of number of through-holes 108. In certain embodiments, sample array 110 may be enclosed in oil and/or between two slides during processing of the samples. In the illustrated embodiment, sample array 110 comprises 48 (4×12) subzones, with each of the 48 fluid dispensers 115 being configured to fill at least one subzone 109.

Fluid dispensers 115, shown in FIGS. 3 and 4, are used to transfer fluid samples into through-holes 108 of sample array 110 and/or into some other suitably configured card, plate, chip, or similar platform. One or more surfaces of fluid dispenser 115 may be treated so as to make the surface more hydrophilic. For example, the inner surface may be plasma treated to be more hydrophilic. Fluid dispenser 115 includes a distal end comprising an opening having a diameter that is from 100 micrometers to 2000 micrometers. In certain embodiments, each fluid dispenser 115 includes a distal end comprising an opening having a diameter that is from 450 micrometers to 550 micrometers. The combination of hydrophilic surfaces and distal end opening diameter may be used to control flow of fluid out of dispenser 115 and into through-holes 108 of sample array 110, for example, providing a capillary effect.

In some embodiment, fluid dispenser 115 comprises a proximal bore 116 and a distal bore 117, the proximal bore 116 being characterized by a first axial length and proximal opening having a first inner diameter and configured to receive the distal end of one of the mandrels. The distal bore 117 may be characterized by a second axial length and a distal opening having a second inner diameter and configured to receive at least a portion of the sample. The first diameter may be between 5 times larger than the second diameter and 10 times larger than the second diameter, for example, to provide favorable stiffness characteristic of the distal portions of fluid dispenser 115 as it moves over the surface of sample array 110. In certain embodiments, favorably stiffness characteristics may be provided when a maximum inner diameter of the distal bore 117 is less than or equal to a minimum inner diameter of the proximal bore 116. In addition, favorably stiffness characteristics may be provided when a ratio of the first axial length to the second axial length is from 0.8 to 1.2.

In certain embodiments, increasing the stiffness of distal portion 117 has been found provide greater accuracy and, therefore, better fluid transfer reliability into through-holes 108 of sample array 110. In such embodiments, contact between the distal opening of distal portion 117 and the surface of sample array 110 are generally a prerequisite to initiating capillary action and flow into through-holes 108 of sample array 110.

Referring again to FIG. 1, a non-limiting example of the various elements of system 100 used in transferring fluid between dispensers 118 and sample array 110 will be described in greater detail. In the illustrated embodiment, the mechanical elements of the system 100 are primarily located within housing 102. When door 105 in closed, enclosure 102 helps protects the sample solutions from debris and contamination. Door 105 may comprise a transparent material or window that provides visual access to the automated processing of one or more sample arrays. For example, door 105 may include a glass or plastic material or window. In certain embodiments, further controls may be implemented to further enhance the environment inside housing 102. For example, the temperature and humidity may be controlled to provide more favorable loading and test results. The control of humidity may be used to reduce evaporation of fluid transferred to sample array 110, thus enabling more than one sample array 110 to be loaded with fluid during a single automated run.

Fluid dispenser holders 118 supply the fluid dispenser 115 used by delivery system 128 during processing. In the illustrated embodiment, there are two fluid dispenser holders 118, with each able to hold enough fluid dispensers 115 to load the delivery system 128 several times during a run to deliver fluid to sample array 110.

Figure 17:
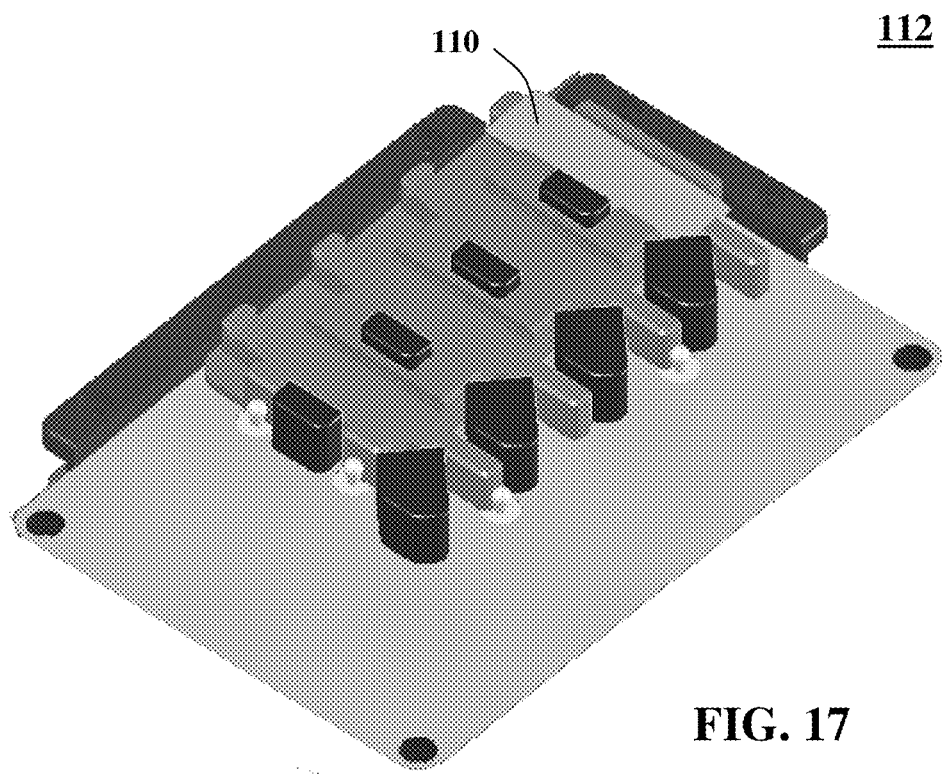
FIG. 17 is a magnified view of sample array platform from the system shown in FIG. 1.

In the illustrated embodiment, sample array platform or support 112 is used to hold and register one or more sample arrays 110. Sample array platform 112 can hold from to one to four sample arrays 110. Referring to FIG. 17, a magnified perspective view is shown for support 112 with one of four available holders containing a sample array 110.

Fluid dispenser registration station or set plate 120 may be used to improve the alignment of fluid dispensers 115 to respective mandrels 132 of delivery system 128 after the fluid dispensers 115 are initially obtained from fluid dispenser holders 118. In particular, set plate 120 may be used to reduce the variation in axial location of the distal tips of each fluid dispenser 115. The increased precision in alignment provided by set plate 120 enables a more uniform contact between the distal tips and the sample array 110, which in turn results in more uniform sample loading into the sample array 110. In certain embodiments, set plate 120 comprises a plurality of wells or holes to receive corresponding fluid dispensers 115. The spacing and dimensions of the wells or holes may be configured to provide a predetermined spacing and relative positioning between tips of the various fluid dispenser holders 118 when the tips are inserted or fitted into the wells or holes. In this manner, the set plate 120 is able to provide a predetermined alignment tolerance between the tips. In some embodiments, the tips of fluid dispensers 115 are tapped a plurality of times or vibrated within the wells or hole of dispenser 115 to provide a predetermined alignment tolerance between the tips.

Fluid dispenser fill station or sample plate 122 contains the sample fluid(s) to be received by fluid dispensers 115 and ultimately delivered to sample array(s) 110.

Disposals bin 125 is configured to receive discarded fluid dispensers 115 that are ejected by stripper 136.

Positioner 138 provides three-dimensional movement of delivery system 128 and fluid dispensers 115 to the various locations or stations within enclosure 102 during operation. Three-dimensional positioner 138 that may be used to move head assembly 130 to various locations during system operation. For example, and as discussed in greater detail below, positioner 138 may be used to move head assembly 130 to the fluid dispenser holder 118 for engagement with a set of fluid dispensers 115 that are loaded with a common sample or with two or more different samples. Subsequently, positioner 138 may be used to move head assembly 130 to sample array platform 112 for transferring the one or more samples contained in fluid dispensers 115, and then moved to disposal bin 125 to dispose of used fluid dispensers 115.

Delivery system 128, when used in conjunction with other elements of system 100, provides a variety functions according to embodiments of the present invention. For example, delivery system 128 may be used to fill fluid set of dispensers 115 with one or more fluids of interest, deliver the one or more fluids to one or more sample arrays, and discard the set of fluid dispensers 115 once they are no longer needed (e.g., to replace some or all of the set of fluid dispensers 115 with different fluid dispensers 115 containing the same or different fluids as contained in a previously used corresponding dispenser).

Figure 7:
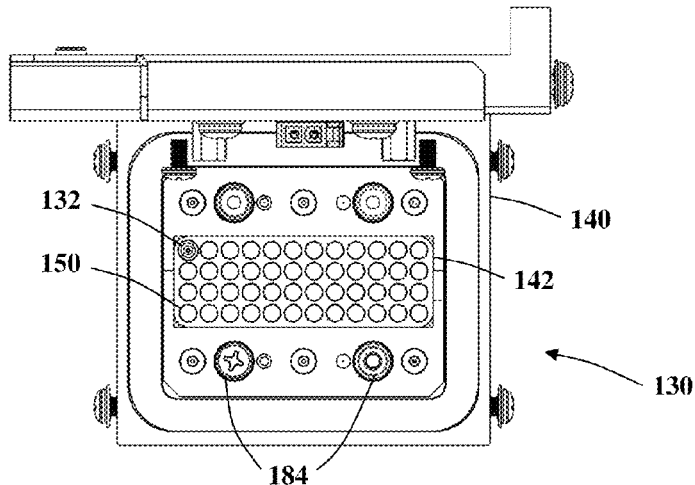
FIG. 7 is a top view of the delivery sub-system shown in FIG. 5.

With added reference to FIGS. 9-11, the construction and function of delivery system 128 will now be given. In illustrated embodiment, head assembly 130 of delivery system 128 comprises frame 140, which is configured, inter alia, to support and/or position head 142. Head 142 comprises a plurality of cylindrical passages or through-holes 150, which are configured to moveably or slidably receive each of mandrels 132. As seen in FIG. 7, head 142 comprises an array of 4×12 through-holes, or a total of 48 through-holes for receiving 48 different mandrels 132. The number of through-holes 150 may be varied according to particular system or functional requirements. For example, head 142 may contain as few as one, two, three, or four through-holes 150 and receive mandrels 132. Alternatively, head 142 may contain a many as 96, 100, 200, or more through-holes 150 and receive mandrels 132.

In certain embodiments each through-hole 150 in head 142 and received mandrel 132 are the same or substantially the same as the remaining through-holes 150 and received mandrels 132. Alternatively, one or more of through-holes 150 and/or received mandrels 132 may be different from others, for example, to accommodate differing requirements for different sample arrays 110 or within different portions or zones of one or more sample arrays 110. For example, some of the mandrels may be configured to hold fluid dispensers 115 that are larger or smaller than others of the fluid dispensers 115.

Head 142 may be fabricated using any of the various techniques or methods know in the art. For example, head 142 may be cast from a mold and through-holes 150 subsequently machined to provide more accurate placement thereof. Alternatively, through-holes 150 may also be cast along with the rest of head 142. Subsequent to casting, through-hole 150 and/or other portions of head 142 may be machined, for example, to provide a more accurate reference and/or to increase the precision of dimensions of through-hole 150 and/or their positions relative to a reference or relative to one another.

Mandrels 132 are configured to moveably or slidably engage a respective one of through-holes 150. Mandrels 132 and through-holes 150 may be dimensioned and/or tolerance to reduce the amount of angular or transfers motion of each mandrel 132 as it traverse through-hole 150. A lubricant may optionally be used to increase the freedom of motion of mandrel 132, for example, to allow a tighter fit of mandrel 132 within through-hole 150 and/or to allow looser tolerance to be held on the diameter of mandrel 132 and/or through-hole 150. In certain embodiments, the aspect ratio of the length to diameter of each through-hole 150 may be selected to provide an amount of rotational or translational motion of mandrels 132 within through-holes 150. For example, in one embodiment, the aspect ratio of the length to diameter of each through-hole 150 is between 6 to 1 and 7 to 1. Alternatively, the aspect ratio of the length to diameter of each through-hole 150 may be at or between 4 to 1 and 10 to 1, or may be at or between 10 to 1 and 20 to 1.

Figure 12:
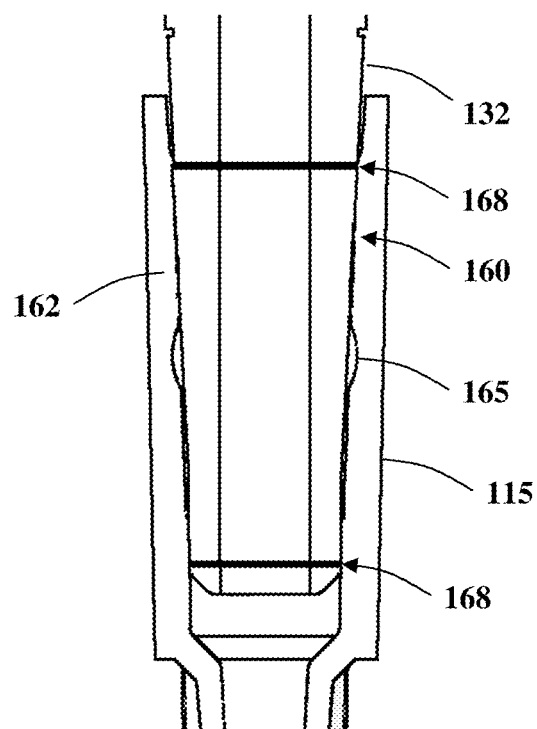
FIG. 12 is a magnified view of the engagement between the fluid dispenser and mandrel portion shown in FIG. 10.

As shown in FIG. 11, mandrel 132 may comprise a counter bore 152 having a diameter configured to receive portions of resilient element 134 and/or a shoulder 155 configured to provide a resting or neutral position for mandrels 132 against a proximal face of block 142. Mandrel 132 may also include a through-hole 158, which may have an inner diameter that is less than the inner diameter of counter bore 152, for example, configured to provide venting of fluid dispensers 115 during operation. With further reference to FIG. 12, distal tip 160 of mandrel 132 may include a shape configured to engage a proximal portion or bore 162 of fluid dispenser 115. For example, distal tip 160 may have taper that is configured to match and/or engage a taper in proximal bore 162 of fluid dispenser 115. In certain embodiments, proximal bore may include one or more portions 165 that are configured to provide a gap between portion(s) 165 and corresponding surface portion(s) of distal tip 160. In certain embodiments, the surfaces of distal tips 160 of one or more mandrels 132 are configured to engage or contact proximal bore 162 at two or more axial locations 168 that are separated by a predetermined value. By making the axial distance between two axial locations 168 relatively large in relation to the bore diameter of proximal bore 162, it has been discovered that the alignment accuracy may be increased between fluid dispenser 115 and mandrel 132. Such alignment accuracy advantageously provides higher precision in locating the distal tip of fluid dispenser 115 at a known location, for example, during transfer of a sample between fluid dispensers 115 and a sample array 110.

Resilient element 134 may also be used, inter alia, to advantageously provide higher precision in locating the distal tip of fluid dispenser 115 at a known location. Referring again to FIG. 11, resilient element 134 is configured to engage mandrel 132 in order to apply a force F thereon in a distal direction. Mandrel 132 is shown in the resting or neutral position, wherein shoulder 155 is pressed against head 142. In the illustrated embodiment shown in FIG. 11, resilient element 134 comprises a base or base plate 170, first spring 172, and second spring 174. In the illustrated embodiment, base plate 170 is coupled or attached to frame 140 of head assembly 130 and is, therefore, fixed relative to head assembly 130 and head 142. In the illustrated embodiment, reference plane 178 is located on the proximal surface of base plate 170; however, reference plane may alternatively be chosen to be a plane passing some other portion of head assembly 130 or a convenient location above or below head assembly 130.

First spring 172 extends between base plate 170 and the bottom of counter bore 152 of mandrel 132 to provide the force F. Second spring 174 is shorter than first spring 172 and sits in the bottom of counter bore 152. The use of second spring 174 will be discussed in greater detail below; however, it will be appreciated that the combined use of first and second springs 172, 174 together provide a non-linear relation between the value of the force F and the distance between base plate 170 and mandrel 132.

Figures 13, 14:
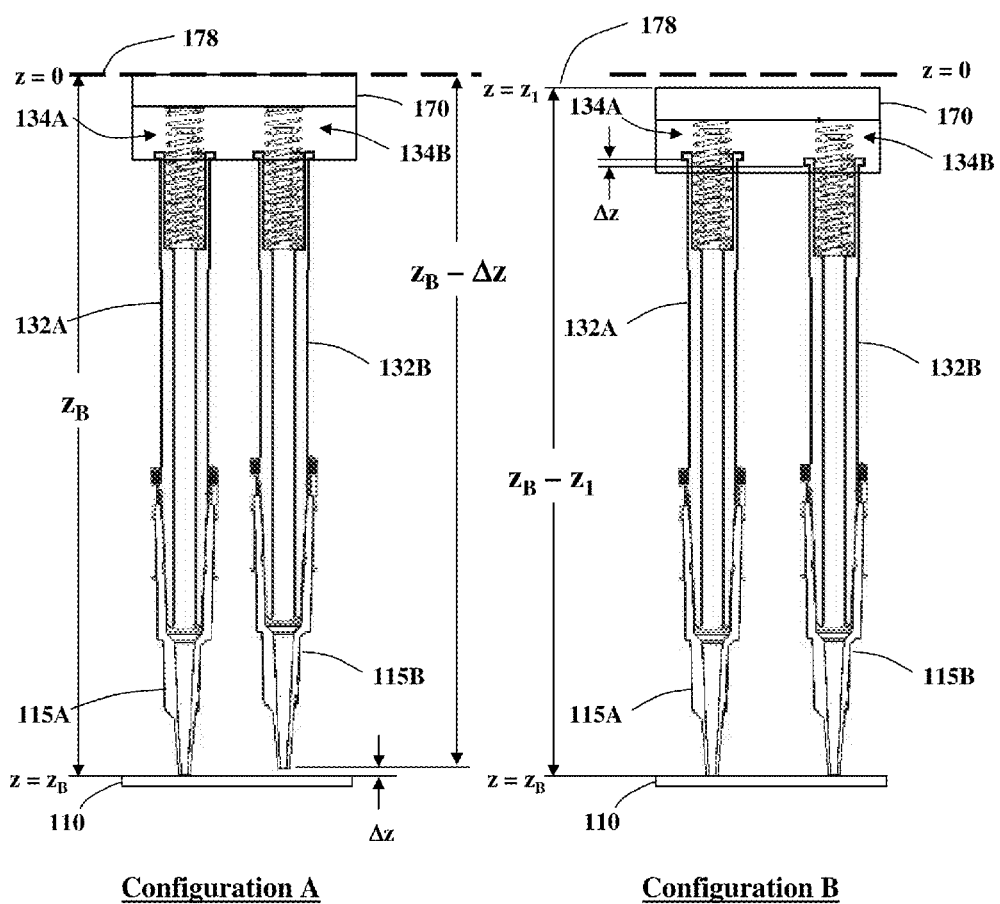
FIGS. 13 and 14 are a partial view of two resilient elements according to an embodiment of the present invention showing the operation thereof.

Referring to FIGS. 13 and 14, the operation and various advantages of resilient element 134 will now be disclosed. FIG. 13a shows Configuration A of system 100, in which two mandrels 132A, 132B are coupled at one end to respective resilient elements 134A, 134B and at the other end to respective fluid dispensers 115A, 115B. Configuration A may be achieved when none of the distal tips of a plurality of fluid dispenser 115 are in contact with a surface. Alternatively, Configuration A may be achieve when only one of the distal tips of a plurality of fluid dispensers (fluid dispenser 115A in the present example) is just barely in contact with a proximal surface of a sample array 110.

As can be seen from FIG. 13, the total length from a single reference plane 178 to the distal end or tip of fluid dispenser 115A is equal to a value of $z_B$. By contrast, the total length from single plane 178 to the distal end or tip of fluid dispenser 115B is equal to a value of $z_B-\Delta z$. The difference in the lengths to the distal ends of 115A and 115B may be attributed to slightly different values of the stacked tolerances in each case, with $z_B$ being a relatively large or maximum length and $z_B-\Delta z$ being a relatively small or minimum length of for the set of mandrel/fluid dispenser combinations 115A, 132A and 115B, 132B.

In certain embodiments, it is advantageous that the distal tips of both fluid dispensers 115A, 115B be contained in a common plane that is parallel to the plane passing through the reference plane at z=0 in FIG. 13. For example, when fluid dispenser 115A, 115B are used to transfer fluid to different areas of sample array 110, it may be necessary that all dispenser tips simultaneously be in contact with top surface of sample array 110 in order to assure transfer of liquid from all dispensers.

With additional reference to FIG. 14, loading system 100 may be used to advantageous achieve this result by placing system 100 in a Configuration B. As can be seen in the figure, by lowering head assembly 130, reference plane 178 is lowered by an amount $z_1$ that is greater than (but be alternatively be equal to) the tolerance stack up difference, $\Delta z$. In this manner, both mandrels 132A, 132B are lifted relative to the proximal surface of head 142 so that a force produced by first springs 172 for each resilient element 134A, 134B is transmitted to the distal tip of fluid dispensers 115A, 115B. As a result, the distal tips of fluid dispensers 115A, 115B are both in contact with the surface of sample array 110, as desired. It will be appreciated that the average force on fluid dispensers 115 is increased in Configuration B as mandrels 132 are displaced further from the proximal surface of head 142. Accordingly, the distance variation between the distal tips of fluid dispensers 115A, 115B have been reduced from a value of $\Delta z$ to a value that is equal to zero or essentially equal to zero. It will be appreciated that, in similar manner, the distal tips of fluid dispenses 115A, 115B may both be made to contact the proximal surface of sample array 110 even when the sample array 110 surface is not perfectly flat.

It will be appreciated that the methodology presented above for fluid dispensers 115A, 115B, my be extended to the larger numbers of fluid dispensers 115, for example, the 48 fluid dispenses 115 of delivery system 128 shown in FIG. 5. In certain embodiments, the length and spring constant for first springs 172 are chosen so that a relatively constant force is produced between a sample array 110 and all 48 of the distal tips fluid dispensers 115 shown in FIG. 5. Additionally or alternatively, the length and spring constant for first springs 172 may be chosen so that the force between sample array 110 and all or most of the distal tips of fluid dispensers 115 is sufficiently low such that friction forces between the sample array 110 surface and the distal tips is below a predetermined value. Such low friction forces have been found to advantageously prevent or reduce bending of the tips. Tip bending due to excessive friction can reduce the accuracy to which the tip position can be determined, which in turn may adversely reduce the effectiveness of transferring fluid to receptacles 108.

In certain embodiments, the variation in length between reference plane 178 and the distal tips of a plurality of more than two fluid dispensers is reduced in Configuration B by at least 50 percent as compared to length variation when system 100 is in Configuration A. In some embodiments, a distance variation is from 5 microns to 5000 microns occurs when a plurality of fluid dispensers 115 are in Configuration A, while the distance variation is less than to 5 microns when the plurality of fluid dispensers 115 are in Configuration B.

As seen in FIGS. 11, 13, and 14, each of resilient elements 134 may also include second spring 174. At least one advantageous use of second spring 174 is to increase the effective spring constant of resilient elements 134 for larger axial displacement of the head assembly 130 from a neutral position such as Configuration A shown in FIG. 13. In certain embodiments, the increase in spring constant may be used to produce larger forces on fluid dispensers 115, for example, to aid in accurately aligning each of the fluid dispensers 115 to a reference coordinate and/or to one another.

In certain embodiments, resilient element 134 additionally or alternatively comprises a first elastically deformable element and a second elastically element. Such elements may, for example, comprise a resilient foam and/or polymer material with a modulus of elasticity suitable for providing a predetermined force verses displacement characteristic. Such elements may replace or supplement the use of springs, such as first and second springs 172, 174. In other embodiments, the resilient element 134 comprises an open loop or closed close electronic system, for example, to provide a non-linear force verses mandrel displacement characteristic.

System 100 further comprises stripper or stripping mechanism 136, which is configured to remove or separate fluid dispensers 115 from corresponding mandrels 132, for example, after all the fluid in a fluid dispenser has been transferred or any remaining fluid in a particular dispenser is not needed. Referring again to FIGS. 6, 8, and 9, stripper 136 includes an upper body or plate 180, a lower body or plate 182, and a plurality of intermediate members 184 disposed between upper and lower plates 180, 182.

In addition, stripper 136 comprises a biasing mechanism including, for example, one or more biasing springs 186 that biases stripper 136 in a proximal configuration, in which lower plate 182 is located at or near head assembly 130 so as expose a relatively large extent of mandrel 132 for coupling to fluid dispenser 115. Stripper 136 also has a distal configuration in which lower plate 182 and upper plate 180 are located more distally than when in the proximal configuration.

Stripper 136 further comprises an electromagnet 188, which may be located in, and is fixed relative to, frame 140 of head assembly 130. During operation, electromagnet 188 has an energized or activated condition in which an electromagnetic field is created and a de-energized or deactivated condition in which electromagnet 188 is turned off and/or has a reduced magnetic field.

In certain embodiments, stripper 136 is in the proximal configuration when electromagnet is in the deactivated condition, wherein it is possible to engage, attach, or couple one or more fluid dispensers 115 to one or more corresponding mandrels 132. In such embodiments, biasing springs 186 maintain lower plate 182 in a proximal position. Upon activation of electromagnet 188, the force produced by biasing springs 186 is overcome a magnetic force on upper and/or lower plates 180, 182, whereby lower plate 182 is maintained in the distal configuration and any fluid dispenses 118 engaged by corresponding mandrel 132 is removed or stripped therefrom.

It will be appreciated that stripper 136 may alternatively be configured such that it is maintained in the proximal configuration when electromagnet is in the activated condition and in the distal configuration whenever electromagnet 188 is in the deactivated condition. In addition, electromagnet 188 and/or upper/lower plates 180, 182 may be replaced by some other force producing configuration. For example, electromagnet 188 may be replaced by a solenoid mechanism and/or a hydraulically activated device.

Stripper 136 may further comprise a plurality of fingers 190 or similar mechanical structure protruding from lower plate 182 that are configured to restrain, impede, or prevent unwanted ancillary fluid dispensers 115 attaching or coupling to mandrels 132, for example, due to a static charge on fluid dispensers surrounding those intended to be engaged by mandrels 132.

Figure 15:
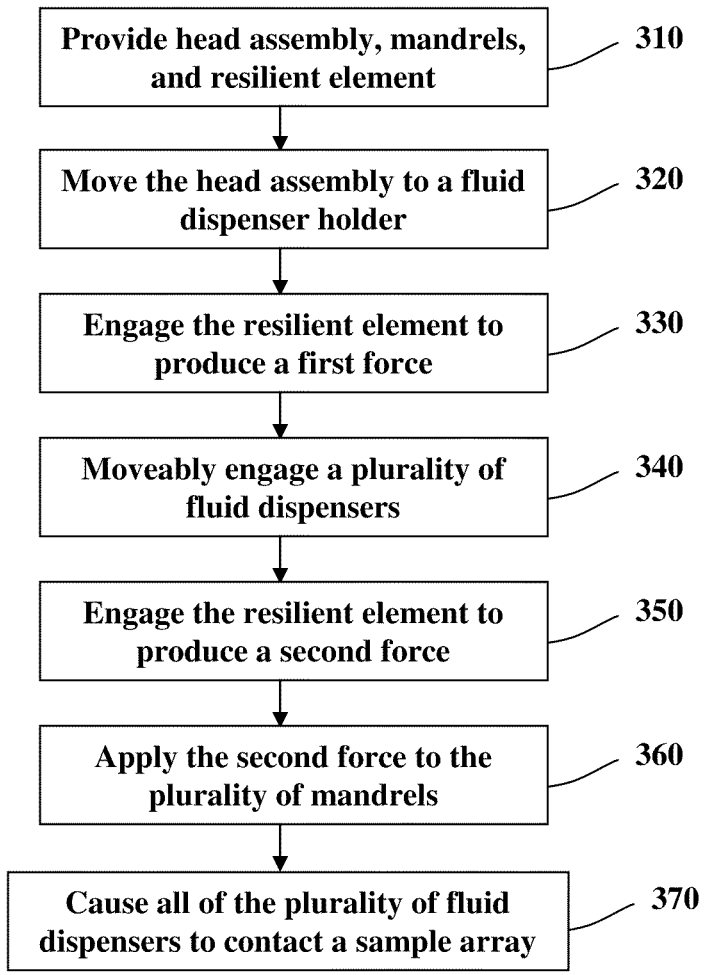
FIG. 15 is a block diagram of a method according to an embodiment of the present invention.

Referring to FIG. 15, in certain embodiments, a method 300 of loading one or more samples into the sample array 110 comprises an element 310 of providing head assembly 130, mandrels 132, and resilient element 134. Method 300 additionally comprises an element 320 of using a positioner, moving the head assembly 130 to a fluid dispenser holder. Method 300 further comprises an element 330 of engaging the resilient element to produce a first force. Method 300 also comprises an element 340 of applying the first force to the plurality of mandrels to moveably engage a plurality of fluid dispensers 115 disposed within the fluid dispenser holder. Method 300 further comprises an element 350 of engaging the resilient element to produce a second force that is less than the first force. Method 300 also comprises an element 360 of applying the second force to the plurality of mandrels. Method 300 additionally comprises an element 370 of wherein the second force is sufficient to cause all of the plurality of fluid dispensers 115 to contact a sample array 110.

Figure 8:
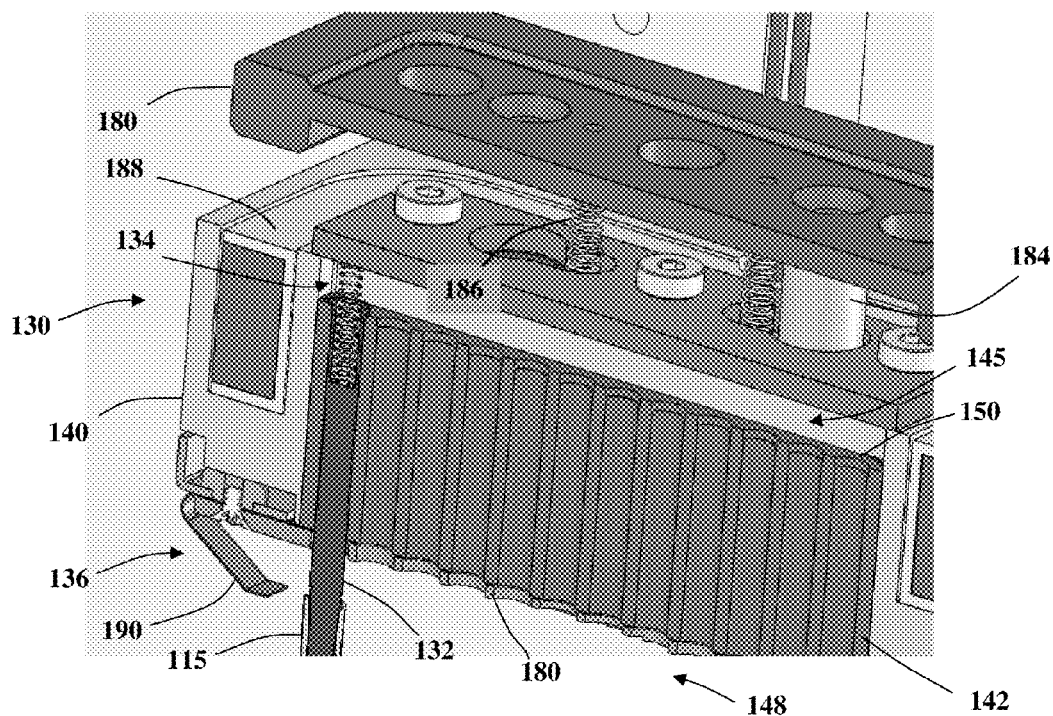
FIG. 8 is a cross-sectional perspective view of the delivery sub-system shown in FIG. 5.

In element 310, method 300 may incorporate of the various embodiments of system 100 disclosed above. In a non-limiting example, method 300 may be use in conjunction with system 100 as shown in FIGS. 1, 8, and 11.

Referring again to FIG. 1, element 320 may include the use of positioner 138 to move the head assembly 130 to fluid dispenser holder 118 is order to engage anywhere from one to 48 fluid dispensers 115. At elements 330 and 340 of method 300, resilient element 134 is used to provide the relatively high force needed for mandrels 132 to engage and align fluid dispensers 115. At elements 350 and 360 of method 300, resilient element 134 is again used produce a force that is sufficiently high to locate the distal tips of each and every fluid holder 118 into contact with the front surface of sample array 110. At the same time, the force produced the tips of fluid dispensers 115 are sufficiently low that there is little or no bending of the distal tips.

This balance or range of forces to accomplish the various tasks necessary to provide accurate automated loading is possible due at least in part to the non-linear nature of resilient element 134. Thus, during transfer of fluid to sample array 110, the relatively low spring constant or modulus of elasticity provides the large amount of axis movement needed in order to even out the slight unevenness of the distal tips of fluid dispensers 115, yet with relatively little variation in the force experienced by the distal tips of each fluid dispenser 115. At the same time, the increased spring constant or modulus of elasticity supplied by the non-linear characteristic when the mandrels travel past a predetermined distance is sufficiently high to avoid bottoming out during elements 330 and 340 when fluid dispensers 118 are being attached an aligned.

At element 370 of method 300, the distal tips of each fluid dispenser 115 are moved across the various surface portions or subzones 109 of sample array 110. Because of the low amount of force used to bring all the distal tips of fluid dispenser 115 into contact with sample array 110, the necessary capillary action provided to induce fluid flow from all of the fluid dispensers 115.

Figure 16:
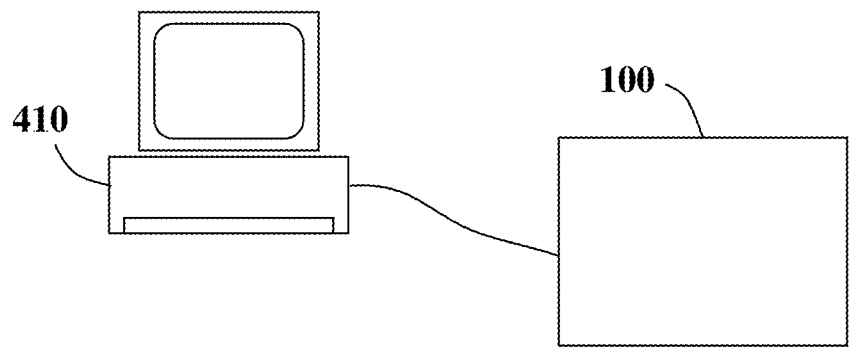
FIG. 16 is a schematic representation of a control and processing system according to an embodiment of the present invention.

With further reference to FIG. 16, schematic representation of a control system 400 including system 100 shown in FIG. 1 and a computer 410 for controlling system 100 during operation and calibration.

Examples of systems in which loaded sample arrays may be analyzed include, but are not limited to, cases and thermocyclers. Exemplary cases and thermocyclers are disclosed in U.S. Pat. No. 7,682,565 and U.S. Published Application No. 20060094108, which are incorporated herein by reference in their entireties.

For instance, U.S. Pat. No. 7,682,565 discloses a system for holding at least one of sample and reagent for analysis. The system includes a pair of parallel covers, at least one of which is light transmissive, of which pair a light transmissive cover forms a top, and of which pair the other forms a bottom. A frame is disposed between the covers to define, in relation to the covers, an interior volume. The frame and the covers are associated with one another to form a case, the case being substantially tight to liquids. A microfluidic array is disposed in the interior volume. The array includes a sheet of material having a pair of opposed surfaces, a thickness, and a plurality of through-holes running through the thickness between the surfaces, the through-holes containing at least one of sample and reagent.

As another example, U.S. Published Application No. 20060094108 discloses a system for thermal cycling a plurality of samples. The system includes a case having a fluid-tight cavity defining an interior volume. A microfluidic array is disposed in the interior volume, the array including a sheet of material having a pair of opposed surfaces, a thickness, and a plurality of through-holes running through the thickness between the surfaces. A thermal cycler having at least one thermally controlled surface is adapted to thermally contact the case.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A loading system, comprising:
an assembly comprising a proximal side and a distal side;
a plurality of mandrels moveably positioned within the assembly;
a plurality of resilient elements, each resilient element disposed inside of and engaging a respective one of the mandrels;
a plurality of fluid dispensers, each fluid dispenser configured to engage a distal end of a corresponding one of the mandrels; and
a sample comprising a solution containing one or more nucleic acid sequences contained within at least one of the fluid dispensers.

2. The loading system of claim 1, wherein the assembly comprises a frame and an insert disposed within the frame, the mandrels moveably positioned within the insert.

3. The loading system of claim 1, wherein the resilient elements are each characterized by a non-linear relationship between a position of the mandrel and a force produced by the resilient element.

4. The loading system of claim 1, wherein each fluid dispenser comprises a distal end, each distal end characterized by an end distance between each distal end and a reference plane located distally from distal ends, the end distance being a distance normal to the reference plane, the end distances of the plurality of fluid dispensers together characterized by an average distance, a minimum distance, a maximum distance, and a distance variation equal to the maximum distance minus the minimum distance, the loading system further comprising:
a first configuration in which the average distance has a first average value and the distance variation has a first variation value; and
a second configuration in which the average distance has a second average value that is less than the first average value and the distance variation has a second variation value that is less than the second variation value.

5. The loading system of claim 4, wherein each of the mandrels has a shoulder and the first configuration is characterized by all the shoulders contacting the assembly.

6. The loading system of claim 1, wherein the resilient element comprises a first elastically deformable element and a second elastically element, the system characterized by:
- a first configuration in which the first elastically deformable element is compressed between the assembly and the mandrel and the second elastically deformable element is uncompressed between the assembly and the mandrel; and
- a second configuration in which the first and second elastically deformable elements are both compressed between the assembly and the mandrel.

7. The loading system of claim 1, wherein the resilient elements comprises a plurality of springs, each spring having a first end engaging a base and a second end engaging a corresponding one of the mandrels.

8. The loading system of claim 1, wherein the resilient elements comprises a first plurality of springs each having a first spring constant and a second plurality of springs each having a second spring constant that is unequal to the first spring constant.

9. The loading system of claim 1, further comprising a stripper, wherein each fluid dispenser has a proximal end and a distal end, the loading system has a plurality of fluid dispensers engaged at the proximal end thereof by the corresponding one of the plurality of mandrels, and the stripper is configured to separate the plurality of fluid dispensers from the plurality of mandrels.

10. The loading system of claim 9, wherein the stripper includes a lower plate disposed in a distal direction from the assembly.

11. The loading system of claim 10, wherein the stripper includes a lower plate disposed in a distal direction from the assembly.

12. The loading system of claim 10, wherein the lower plate includes a plurality of through-holes and each mandrel is located within one of the plurality of through-holes of the lower plate.

13. The loading system of claim 1, wherein each fluid dispenser comprises at least an inner surface that is treated so as make the at least inner surface more hydrophilic.

14. The loading system of claim 1, wherein each fluid dispenser includes a distal end comprising an opening having a diameter that is from 450 micrometers to 550 micrometers.

15. The loading system of claim 8, wherein each spring of the second plurality of springs is disposed inside a respective one of the first plurality of springs.

* * * * *